(12) United States Patent
Kim et al.

(10) Patent No.: US 10,995,153 B2
(45) Date of Patent: May 4, 2021

(54) POLYPEPTIDE SELECTIVELY BINDING TO IMMUNOGLOBULIN G OF MOUSE OR RABBIT AND USE THEREOF

(71) Applicant: KOREA ADVANCED INSTITUTE OF SCIENCE AND TECHNOLOGY, Daejeon (KR)

(72) Inventors: Hak-Sung Kim, Daejeon (KR); Sukyo Jeong, Daejeon (KR); Woosung Heu, Daejeon (KR); Jong-Won Kim, Daejeon (KR); Joong-Jae Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 359 days.

(21) Appl. No.: 16/074,530

(22) PCT Filed: Sep. 20, 2016

(86) PCT No.: PCT/KR2016/010461
§ 371 (c)(1),
(2) Date: Aug. 1, 2018

(87) PCT Pub. No.: WO2017/135545
PCT Pub. Date: Aug. 10, 2017

(65) Prior Publication Data
US 2019/0040157 A1    Feb. 7, 2019

(30) Foreign Application Priority Data
Feb. 1, 2016  (KR) ........................ 10-2016-0012183

(51) Int. Cl.
| | | |
|---|---|---|
| C07K 16/46 | (2006.01) |
| C07K 14/195 | (2006.01) |
| C12N 15/62 | (2006.01) |
| C12N 15/63 | (2006.01) |
| G01N 33/531 | (2006.01) |
| G01N 33/543 | (2006.01) |
| C12N 15/70 | (2006.01) |
| G01N 33/532 | (2006.01) |
| C07K 14/705 | (2006.01) |
| G01N 33/544 | (2006.01) |

(52) U.S. Cl.
CPC .......... *C07K 16/468* (2013.01); *C07K 14/195* (2013.01); *C07K 14/705* (2013.01); *C07K 16/464* (2013.01); *C12N 15/62* (2013.01); *C12N 15/63* (2013.01); *C12N 15/70* (2013.01); *G01N 33/531* (2013.01); *G01N 33/532* (2013.01); *G01N 33/544* (2013.01); *G01N 33/54306* (2013.01)

(58) Field of Classification Search
CPC ............................ C07K 16/468; C07K 16/464
See application file for complete search history.

(56) References Cited

U.S. PATENT DOCUMENTS

| | | |
|---|---|---|
| 2014/0243210 A1 | 8/2014 | Carbonell et al. |
| 2014/0274790 A1 | 9/2014 | Ito |

FOREIGN PATENT DOCUMENTS

| | | |
|---|---|---|
| KR | 1020120019927 A | 3/2012 |
| KR | 20150007077 A | 1/2015 |

OTHER PUBLICATIONS

Lee, S., et al., "Design of a Binding Scaffold Based on Variable Lymphocyte Receptors of Jawless Vertebrates by Module Engineering", "Proceedings of the National Academy of Sciences", Feb. 28, 2012, pp. 3299-3304, vol. 109, No. 9.

Zhang, Y., et al., "Specificity and Regenerability of Short Peptide Ligands Supported on Polymer Layers for Immunoglobulin G Binding and Detection", "ACS Applied Materials and Interfaces", Jul. 8, 2013, pp. 8030-8037, vol. 5, No. 8, Publisher: American Chemical Society.

*Primary Examiner* — Amy E Juedes
*Assistant Examiner* — Brian Hartnett
(74) *Attorney, Agent, or Firm* — Hultquist, PLLC; Steven J. Hultquist

(57) ABSTRACT

The present invention relates to a novel polypeptide that binds selectively to mouse or rabbit immunoglobulin G. More specifically, the present invention relates to a polypeptide that binds to mouse or rabbit immunoglobulin G, a polynucleotide encoding the polypeptide, an expression vector comprising the polynucleotide, a transformant introduced with the expression vector, a method of producing the polypeptide using the transformant, and a composition for immunoassay comprising the polypeptide. The novel peptide according to the present invention binds specifically to mouse or rabbit immunoglobulin G, can replace conventional expensive secondary immunoglobulin G, and can be used in various biological immunoassays. In addition, a conjugate of the polypeptide of the present invention and immunoglobulin G is useful for fabrication of various immunosensors/immunochips and for drug screening.

13 Claims, 4 Drawing Sheets
Specification includes a Sequence Listing.

POLYPEPTIDE SELECTIVELY BINDING TO IMMUNOGLOBULIN G OF MOUSE OR RABBIT AND USE THEREOF

CROSS-REFERENCE TO RELATED APPLICATIONS

This is a U.S. national phase under the provisions of 35 U.S.C. § 371 of International Patent Application No. PCT/KR16/10461 filed Sep. 20, 2016, which in turn claims priority of Korean Patent Application No. 10-2016-0012183 filed Feb. 1, 2016. The disclosures of such international patent application and Korean priority patent application are hereby incorporated herein by reference in their respective entireties, for all purposes.

TECHNICAL FIELD

The present invention relates to a novel polypeptide that binds specifically to mouse or rabbit immunoglobulin G, and more particularly to a polypeptide that binds specifically to mouse or rabbit immunoglobulin G, a method for producing the polypeptide, and an immunoassay composition comprising the polypeptide.

BACKGROUND ART

Immunoglobulin is a glycoprotein that functions as an antibody that neutralizes external antigens such as viruses and bacteria. It is found in blood or tissue fluids. Immunoglobulin G is the most abundant immunoglobulin, and is an important substance that protects the body by invoking an immune response by binding with exogenous substances.

Binding between immunoglobulin G and an exogenous substance is called an immune response. Using this characteristic, primary immunoglobulin G that recognizes a specific antigen is produced, and secondary immunoglobulin G that binds to primary immunoglobulin G is produced by an immunological reaction of mice or rabbits which are most frequently used as animal species. The produced immunoglobulins G are used in biological immunoassays.

However, in the production of secondary immunoglobulin G that binds to primary immunoglobulin G, there are problems in terms of the use of experimental animals and the time and costs necessary for hybridoma production and culture. In addition, a post-treatment process is required to link the enzyme and fluorescent marker for signal detection by a chemical reaction. In this process, a problem arises in that the efficiency of the final product is reduced due to the structural instability of secondary immunoglobulin G. In addition, the limit of detection appears due to the non-specific reactivity and cross-reactivity of secondary immunoglobulin G.

Under this background, the present inventors have designed a novel polypeptide capable of substituting for conventional secondary immunoglobulin G by use of the protein repebody. The repebody means a polypeptide prepared by fusion of the N-terminus of internalin B having a leucine-rich repeat (LRR) structure and VLR based on the structural similarity therebetween so as to have an optimal consensus design. The repebody has a size equal ⅕ of that of antibody, and can be produced in *Escherichia coli* in large amounts at low costs, and has very high thermal and pH stabilities. Thus, it is highly advantageous for industrial applications. In addition, it was demonstrated that the binding affinity of the repebody for a target substance could be easily increased to picomole levels and had very high specificity for a target substance.

The present inventors previously developed a repebody that binds specifically to human immunoglobulin G (Korean Patent Application No. 10-2013-0081009). However, the developed repebody has a disadvantage in that it has specificity only for human immunoglobulin G and does not bind to mouse or rabbit immunoglobulin G which is generally used in biological immunoassays.

Accordingly, the present inventors have made extensive efforts to solve the above-described problems and to develop a protein that binds specifically to mouse or rabbit immunoglobulin G (specific protein binder), and as a result, have found that when a mutation library is constructed using repebodies and a novel polypeptide having a specific binding affinity for mouse or rabbit immunoglobulin G is screened by module-based affinity amplification, the screened repebody exhibits better effects than conventional immunoglobulin G in various immunoassays, thereby completing the present invention.

DISCLOSURE OF INVENTION

Technical Problem

It is an object of the present invention to provide a repebody binding selectively to rabbit or mouse immunoglobulin G; a polynucleotide encoding the above-described repebody; an expression vector comprising the above-described polynucleotide; a recombinant microorganism into which the above-described expression vector is introduced; and a method of producing the above-described repebody by use of the above-described recombinant microorganism.

Another object of the present invention is to provide a method of immobilizing or purifying rabbit or mouse immunoglobulin G by use of the above-described repebody.

Still another object of the present invention is to provide a composition for immunoassay containing the above-described repebody.

Technical Solution

To achieve the above object, the present invention provides a repebody comprising any one of the amino acid sequences represented by SEQ ID NOS: 3 and 7 to 12, the repebody binding selectively to rabbit immunoglobulin G.

The present invention also provides a polynucleotide encoding the above-described repebody.

The present invention also provides a recombinant vector comprising the above-described polynucleotide.

The present invention also provides a recombinant microorganism into which the above-described polynucleotide or the above-described recombinant vector is introduced.

The present invention also provides a method for producing a repebody, wherein the method comprises: (i) expressing a repebody by culturing the above-described recombinant microorganism; and (ii) recovering the expressed repebody.

The present invention also provides a method for purifying a rabbit immunoglobulin G antibody, wherein the method comprises the steps of: (i) injecting a mixture comprising a rabbit immunoglobulin G antibody into a column into which the above-described repebody is adsorbed; and (ii) eluting the antibody attached to the column of step (i).

The present invention also provides a method for immobilizing rabbit immunoglobulin G, wherein the method comprises the steps of: (i) treating the surface of a solid substrate by attaching the above-described repebody onto the solid substrate; and (ii) binding rabbit immunoglobulin G to the surface-treated solid substrate.

The present invention also provides an immunosensor in which rabbit immunoglobulin G is immobilized onto a solid substrate surface-treated with the above-described repebody, using the repebody as a mediator.

The present invention also provides a method of detecting a substance having binding affinity for rabbit immunoglobulin G by use of the repebody of the present invention, the method comprising the steps of: (a) treating the above-described immunosensor with a sample containing the substance having binding affinity for rabbit immunoglobulin G; and (b) determining whether the substance would bind to the immunosensor.

The present invention also provides a composition for ELISA; a composition for Western blotting; and a composition for immunohistochemical staining of rabbit immunoglobulin G, the composition comprising the above-described repebody.

The present invention also provides a repebody comprising any one of the amino acid sequences represented by SEQ ID NOS: 4 to 6 and 13 to 15, the repebody binding selectively to mouse immunoglobulin G.

The present invention also provides a polynucleotide encoding the above-described repebody.

The present invention also provides a recombinant microorganism into which the above-described polynucleotide or the above-described recombinant vector is introduced.

The present invention also provides a method for producing a repebody, wherein the method comprises: (i) expressing a repebody by culturing the above-described recombinant microorganism; and (ii) recovering the expressed repebody.

The present invention also provides a method for purifying a mouse immunoglobulin G antibody, wherein the method comprises the steps of: (i) injecting a mixture comprising a mouse immunoglobulin G antibody into a column into which the above-described repebody is adsorbed; and (ii) eluting the antibody attached to the column of step (i).

The present invention also provides a method for immobilizing mouse immunoglobulin G, wherein the method comprises the steps of: (i) treating the surface of a solid substrate by attaching the above-described repebody onto the solid substrate; and (ii) binding mouse immunoglobulin G to the surface-treated solid substrate.

The present invention also provides an immunosensor in which mouse immunoglobulin G is immobilized onto a solid substrate surface-treated with the above-described repebody, using the repebody as a mediator.

The present invention also provides a method of detecting a substance having binding affinity for mouse immunoglobulin G by use of the repebody of the present invention, the method comprising the steps of: (a) treating the above-described immunosensor with a sample containing the substance having binding affinity for mouse immunoglobulin G; and (b) determining whether the substance would bind to the immunosensor.

The present invention also provides a composition for ELISA; a composition for Western blotting; and a composition for immunohistochemical staining of mouse immunoglobulin G, the composition comprising the above-described repebody.

BEST MODE FOR CARRYING OUT THE INVENTION

Figure 1:
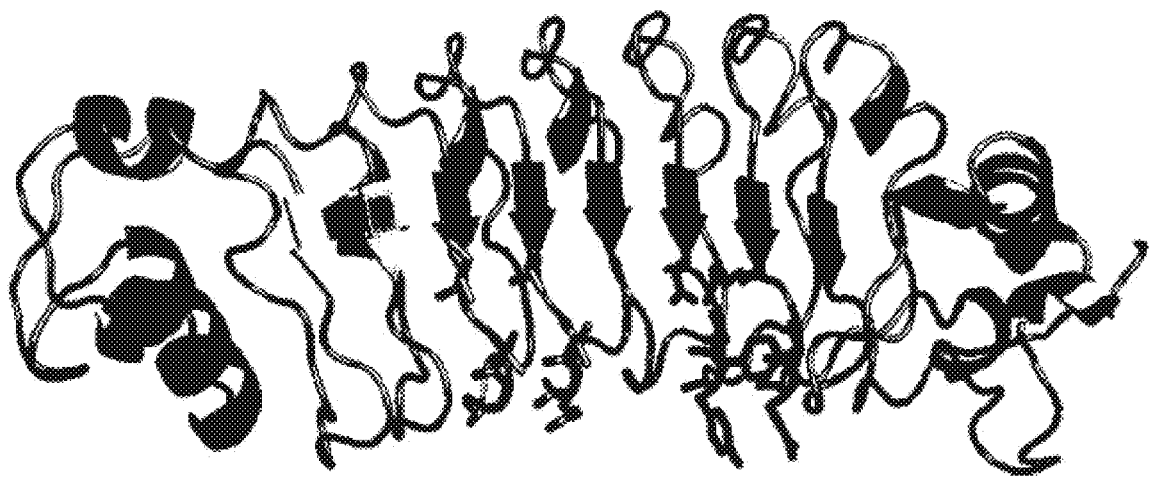
FIG. 1 is a schematic view showing an overall structure that represents amino acid residues in random libraries constructed in the present invention in order to develop repebodies that bind to rabbit immunoglobulins G.

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, a polypeptide that binds specifically to mouse or rabbit immunoglobulin G was screened, and the immunological application thereof was evaluated.

In the present invention, polypeptides contained in libraries for repebody development were subjected to biopanning using phagemids of mouse or rabbit immunoglobulin G, thereby selecting polypeptides that bind specifically to mouse or rabbit immunoglobulin G, and the work to improve the binding affinities of the selected polypeptides was performed. As a result, polypeptides that bind specifically to mouse or rabbit immunoglobulin G were obtained.

In other words, in one example of the present invention, In order to develop a novel polypeptide capable of binding specifically to rabbit or mouse immunoglobulin G, the present inventors have constructed a library that randomly contains the repeat modules of a polypeptide that comprises a fusion of the N-terminus of internalin B protein and the leucine-rich repeat (LRR) protein domain of variable lymphocyte receptor (VLR). The polypeptide contained in the library for the development of the repebody binding to rabbit immunoglobulin G may be encoded by a polynucleotide sequence of SEQ ID NO: 1 or a polynucleotide sequence having a homology of 75%, preferably 85%, more preferably 90%, further preferably 95% or more, with the polynucleotide sequence of SEQ ID NO: 1. The polypeptide contained in the library for the development of the repebody binding to mouse immunoglobulin G may be encoded by a polynucleotide sequence of SEQ ID NO: 2 or a polynucleotide sequence having a homology of 75%, preferably 85%, more preferably 90%, further preferably 95% or more, with the polynucleotide sequence of SEQ ID NO: 2.

In addition, the library may be formed of phagemid including the polynucleotide. In the present invention, the term "phagemid" means a circular polynucleotide molecule derived from a phage which is a virus having E. coli as a host and includes sequences of proteins and surface-proteins required for propagation and proliferation. A recombinant phagemid may be produced using gene recombinant technology well known in the art, and site-specific DNA cleavage and connection may be performed by an enzyme, generally known in the art, and the like. The phagemid may include a signal sequence or leader sequence for secretion in addition to expression regulating factors such as a promoter, an operator, an initiation codon, a termination codon, an enhancer and may be mainly used in a method for labeling the protein on a surface of the phage by fusing a desired protein with a surface protein of the phage. The promoter of the phagemid is mostly inducible and may include a selective marker for selecting a host cell. For an object of the present invention, the phagemid may be a polynucleotide of SEQ ID NO: 2 described in the prior Korean patent 10-2012-0019927 of the present inventors, including MalEss, DsbAss or PelBss which is a signal sequence or a leader sequence for expressing and secreting the polypeptide-encoding polynucleotide constructing the library, and including a histidine-tag for confirming expression of a recombinant protein on a surface of the phage, and a polynucleotide which encodes gp3 domain which is a kind of a surface protein of M13 phage for expression on the surface of the phage, but the present invention is not particularly limited thereto.

Figure 2:
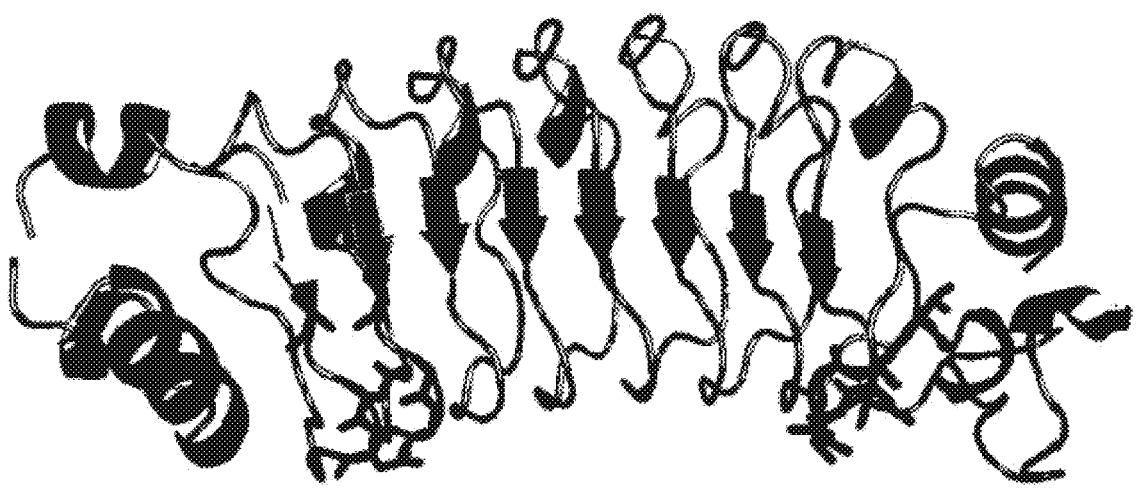
FIG. 2 is a schematic view showing an overall structure that represents amino acid residues in random libraries constructed in the present invention in order to develop repebodies that bind to mouse immunoglobulins G.
Figure 3:
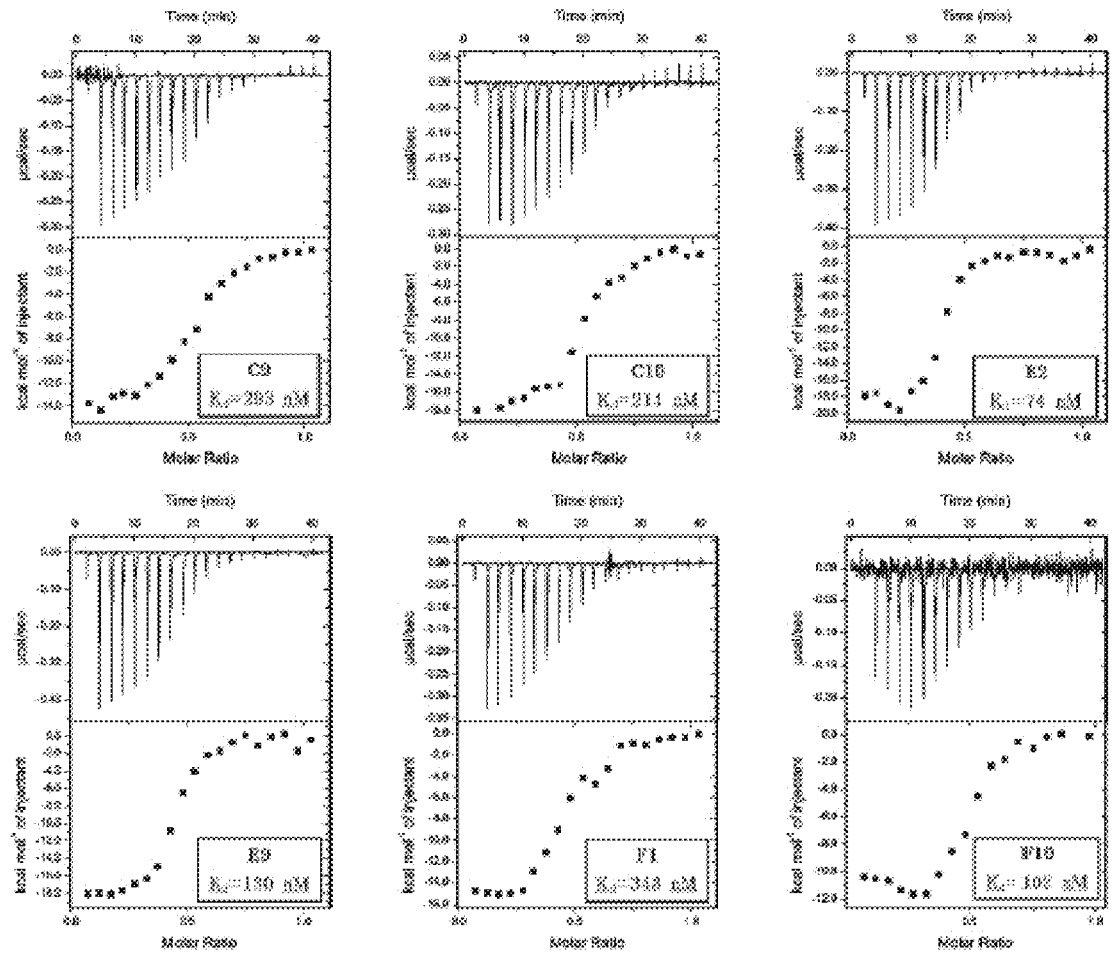
FIG. 3 shows the results of isothermal titration calorimetry (ITC) performed to measure the binding affinities of repebody clones finally selected after performing phage display biopanning for rabbit immunoglobulins G by use of the phage libraries constructed in the present invention.

The present inventors have selected repebody-type novel polypeptides (SEQ ID NO: 3) having high binding affinities for rabbit immunoglobulin G by use of a phage display method employing a library corresponding to SEQ ID NO: 1 containing the phagemids. In addition, the present inventors have selected repebody-type novel polypeptides (SEQ ID NOs: 4 to 6) having high binding affinities for mouse immunoglobulin G by use of a phage display method employing a library corresponding to SEQ ID NO: 2 containing the phagemids (FIGS. 1 to 3).

Thereafter, site-directed mutagenesis has been performed in order to increase the binding affinities for the rabbit immunoglobulin G, and as a result, novel polypeptides having increased binding affinities (SEQ ID NOS: 7 to 12) have been selected. In addition, site-directed mutagenesis has been performed in order to increase the binding affinities for the mouse immunoglobulin G, and as a result, novel polypeptides having increased binding affinities (SEQ ID NOS: 13 to 15) have been selected. Thus, it could be found that the binding affinities for the rabbit or mouse immunoglobulin G are very high (FIGS. 1 to 4).

Therefore, in one aspect, the present invention is directed to a repebody comprising any one of the amino acid sequences represented by SEQ ID NOS: 3 and 7 to 12, the repebody binding selectively to rabbit immunoglobulin G.

The present invention is also directed to a repebody comprising any one of the amino acid sequences represented by SEQ ID NOS: 4 to 6 and 13 to 15, the repebody binding selectively to mouse immunoglobulin G.

In the present invention, the term "repebody" is a polypeptide optimized by consensus design through fusion of the N-terminal of the internalin B having the LRR protein structure and the VLR based on the structural similarity. The repebody protein may be structurally divided into a concave region and a convex region (FIGS. 1 and 2). Here, it is known that the concave region has high variety of the sequence and is important in protein interaction. On the contrary, the convex region serves to stably maintain the entire structure of protein based on the highly conserved sequence. The repebody protein may include all fusion LRR family protein obtained by using all proteins included in the LRR family having the repeat module to improve the solubility expression and biophysical properties of protein of all protein by the above-described method.

In the present invention, the term "variable Lymphocyte Receptor (VLR)" refers to a kind of the LRR family protein that is expressed and performs an immune function in hagfishes and lampreys, and is usefully used as a backbone capable of binding to various antigenic substances. A polypeptide in which the N-terminal of the internalin B protein and the VLR protein are fused is relatively increased in solubility and expression amount as compared to a VLR Protein that is not fused with the internalin B protein, and thus can be used in the preparation of a novel protein therapeutic agent based on the increase of solubility and expression amount.

As used herein, the term "Leucine rich repeat (LRR) family protein" means a protein formed by combination of modules in which leucine is repeated at a certain position, (i) it has one or more LRR repeat modules, (ii) the LRR repeat module consists of 20 to 30 amino acids, (iii) the LRR repeat module has "LxxLxxLxLxxN" as a conservation pattern, wherein L means hydrophobic aminoacids such as alanine, glycine, phenylalanine, tyrosine, leucine, isoleucine, valine, and tryptophan; N means asparagine, glutamine, serine, cysteine or threonine and x means any amino acid, and (iv) the LRR family protein means a protein having a three dimensional structure like horseshoe. The LRR family protein of the present invention may include all mutants having the sequence which is already known or found by mRNA or cDNA newly induced in vivo, as well as the sequence which is not known in the natural world through consensus design, and the like, and having a frame of the repeat module.

In the present invention, the term "internalin B protein" is a kind of the LRR family protein expressed in a *Listeria* strain, and it is known that the internalin B protein has an N-terminal structure different from that of the LRR family proteins in which a hydrophobic core are uniformly distributed through the entire molecule to thereby be stably expressed in microorganisms. It is considered that since the N-terminal of the internalin protein which is the most important in folding a repeat module is derived from a microorganism and has a stable shape including an alpha-helix, such that the internalin protein can be effectively used for stable expression of LRR family proteins in microorganisms.

In the present invention, the term "N-terminal of an (or the) internalin protein" of the present invention means an N-terminal of the internalin protein required for soluble expression and folding of the protein, and means a repeat module of the alpha-helix capping motif and the internalin protein. The N-terminal of the internalin protein may limitlessly include any N-terminal of the internalin protein required for soluble expression and folding of the protein, and as an example thereof, an alpha-helix capping motif "ETITVSTPIKQIFPDDAFAETIKANLKKKSVT-DAVTQNE" and the repeat module may be included. The repeat module pattern may be "LxxLxxLxLxxN". In the repeat module patttern, L means alanine, glycine, phenylalanine, tyrosine, leucine, isoleucine, valine, or tryptophan; N means asparagine, glutamine, serine, cysteine or threonine; and x means any hydrophilic amino acid. In addition, the N-terminal of the internalin protein of the present invention may be selected and used as long as the N-terminal has a high structural similarity depending on a kind of the LRR family protein that can be fused, and the most stable amino acid may be selected by calculation of a binding energy, and the like, and the amino acid of the module corresponding thereto may be mutated.

As used herein, the term "Immunoglobulin G (IgG)" is one kind of a globulin protein having an antibody activity, which is contained in body fluids such as serum and the like, and accounts for approximately 70% of the immunoglobulin. Immunoglobulin G is a glycoprotein having a molecular weight of about 160,000 Da and building the Y-shaped molecular model. Two upper ends of Immunoglobulin G bind to an antigen and a lower end (Fc region) thereof allows an antibody binding to the antigen to bind to complement or cells so as to have a biological activity. In addition, immunoglobulin G is involved in overall immune responses to cause neutralization, precipitation, and flocculation of toxins or viruses.

In another aspect, the present invention is directed to a polynucleotide encoding the above-described repebody; a recombinant vector comprising the above-described polynucleotide; and a recombinant microorganism.

In the present invention, the polynucleotide may be a polynucleotide encoding any one amino acid sequence of SEQ ID NOS: 3 to 15, and may be a polynucleotide having a base sequence having a homology of 70% or more, more preferably 80% or more, and more preferably 90% or more, with the polynucleotide, but is not particularly limited thereto.

As used herein, the term "vector" refers to a DNA construct containing the nucleotide sequence of a target protein-encoding gene operably linked to a suitable regulatory sequence so as to be able to express the target gene in a suitable host cell. The regulatory sequence includes a promoter capable of initiating transcription, any operator for regulating this transcription, a sequence encoding a suitable mRNA ribosome binding site, and a sequence for regulating the termination of transcription and translation. Once transformed into a suitable host, the vector may replicate or function independently of the host genome, or may integrate into the genome itself.

The vector used in the present invention is not particularly limited as long as it is capable of being replicated in host cells, and may be any vector known in the art. Examples of the vector that is generally used may include plasmid, phagemid, cosmid, virus, and bacteriophage in a natural state or in a recombinant state. For example, as the phage vector or the cosmid vector, pWE15, M13, λMBL3, λMBL4, λIXII, λASHII, λAPII, λt10, λt11, Charon4A, and Charon21A, etc., may be used, and as the plasmid vector, pBR-based, pUC-based, pBluescriptII-based, pGEM-based, pTZ-based, pCL-based and pET-based, etc., may be used. The vector usable in the present invention is not particularly limited, but may be any known expression vector. Preferably, pACYC177, pACYC184, pCL, pECCG117, pUC19, pBR322, pMW118, pCC1BAC, pET-21a, pET-32a vectors, etc., may be used. Most preferably, the pET-21a vector and the pET-32a vector may be used.

In the present invention, the term "recombinant microorganism" means a transfected cell in which a vector having a gene encoding one or more target proteins is introduced into a host cell to express the target protein, and may include all cells such as eukaryotic cells, prokaryotic cells, and the like. Examples thereof may include bacteria cells such as *E. coli, streptomyces, Salmonella Typhimurium*, and the like; yeast cells; fungus cells such as *pichiapastoris*, and the like; insect cells such as *drosophila, spodoptera* Sf9 cell, and the like; animal cells such as CHO, COS, NSO, 293, bow melanoma cell; or plant cells, but the present invention is not particularly limited thereto. A host cell that may be used in the present invention is not particularly limited, but *E. coli* may preferably be used as a host cell. Most preferably, *E. coli* BL21 (DE3) or OrigamiB (DE3) may be used as a host cell.

As used herein, the term "transformation" means introducing a vector comprising a polynucleotide encoding a target protein into a host cell so as to be able to express a protein encoded by the polynucleotide in the host cell. The transformed polynucleotides include all the genes inserted in the chromosome of the host cell or located outside the chromosome, as long as they can be expressed in the host cell. In addition, the polynucleotides include DNA and RNA, which encode the target protein. As long as the polynucleotide can be introduced in the host cell and expressed therein, the gene may be introduced in any form. For example, the polynucleotide can be introduced into the host cell in the form of an expression cassette which is a polynucleotide construct including all elements for expressing the gene. The expression cassette includes a promoter which is operably linked to the gene, a transcription termination signal, a ribosome binding site, and a translation termination signal. The expression cassette may be in the form of an expression vector capable of self-replicating. The polynucleotide may also be introduced into the host cell by itself, and be operably linked to the sequence necessary for expression in the host cell.

In still another aspect, the present invention is directed to a method for producing a repebody, wherein the method comprises: (i) expressing a repebody by culturing the above-described recombinant microorganism; and (ii) recovering the expressed repebody.

In the method, the culturing of the recombinant microorganism may be preferably performed by a batch culture method, a continuous culture method, a fed-batch culture, and the like, known in the art, but the present invention is not particularly limited thereto, wherein under culture conditions, pH may be appropriately adjusted (pH 5 to 9, preferably pH 6 to 8, most preferably pH 6.8) by using a basic compound (for example: sodium hydroxide, potassium hydroxide or ammonia) or an acidic compound (for example, phosphoric acid or sulfuric acid), and an aerobic condition may be maintained by introducing oxygen, or an oxygen-containing gas mixture into the culture, and the culture may be performed at 20 to 45° C., preferably, 25 to 40° C. for about 10 to 160 hours. The polypeptide produced by the culture may be secreted in the medium or remained in the cell.

In addition, in the culture medium used, as carbon source, sugar and carbohydrate (for example, glucose, sucrose, lactose, fructose, maltose, molasse, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing; as nitrogen source, nitrogen-containing organic compound (for example, peptone, yeast extract, gravy, malt extract, corn steep liquor, soybean meal powder and urea), or inorganic compound (for example, ammonium sulfate, ammonium chloride, ammonium phosphate, ammonium carbonate and ammonium nitrate) and the like, may be used individually or by mixing; as phosphate source, potassium dihydrogen phosphate, dipotassium hydrogen phosphate, sodium-containing salt corresponding thereof, and the like, may be used individually or by mixing; or essential growth-promoting materials such as other metal salts (for example, magnesium sulfate or iron sulfate), amino acids and vitamins may be included.

In the recovering of the repebody produced in the culturing of the present invention, the desired polypeptide may culturing of the present invention, the desired repebody may be recovered from a culture fluid by appropriate culture methods such as a batch culture method, a continuous culture method, a fed-batch culture, and the like, known in the art.

In the meantime, it was expected that when the repebody of the present invention will be utilized for various immoassays and the purification of rabbit or mouse immunoglobulin G.

In another example of the present invention, a repebody-enzyme conjugate or a repebody-quantum dot conjugate was prepared, and then applied to an immunoassay. As a result, it could be found that the repebody-enzyme conjugate or the repebody-quantum dot conjugate exhibits significantly higher accuracy and sensitivity compared to a conventional secondary immunoglobulin G-enzyme conjugate or secondary immunoglobulin G-quantum dot conjugate(FIGS. 5 to 8).

In still another aspect, the present invention is directed to a method for purifying a rabbit or mouse immunoglobulin G antibody, wherein the method comprises the steps of: (i) injecting a mixture comprising a rabbit or mouse immunoglobulin G antibody into a column onto which the repebody according to the present invention is adsorbed; and (ii) eluting the antibody attached to the column of step (i).

Here, a bead onto which the repebody is attached may be packed into a column instead of directly adsorbing the repebody onto the column in the step (i) above. The repebody according to the present invention may comprise any one of the amino acid sequence of SEQ ID NOs: 3 and 7 to 12 in case of rabbit, and may comprise any one of the amino acid sequence of SEQ ID NOs: 4 to 6 and 13 to 15 in case of mouse.

In still another aspect, the present invention is directed to a method for immobilizing rabbit or mouse immunoglobulin G, wherein the method comprises the steps of: (i) treating the surface of a solid substrate by attaching the repebody according to the present invention onto the solid substrate; and (ii) binding rabbit or mouse immunoglobulin G to the surface-treated solid substrate. The repebody according to the present invention may comprise any one of amino acid sequences of SEQ ID NOS: 3 and 7 to 12 in case of rabbit, and may comprise any one of amino acid sequences of SEQ ID NOS: 4 to 6 and 13 to 15 in case of mouse.

In the method, the solid substrate may be selected from a group consisting of a CM-5 Au sensor chip, a magnetic micro bead, a glass plate, a gold nanoparticle, a biodegradable organic polymer nanoparticle such as PLGA, and various kinds of micro well plates. IgG used in the present invention is preferably human IgG, but is not limited thereto. By the surface-treating of the step (i) above, the solid substrate may be bound to protein so that orientation is controlled and may have an increased uniformity on a surface thereof. The method of immobilizing IgG using the repebody of the present invention may be physically and chemically stable and may have a significantly wide use thereof as compared to the existing method of using antibody-binding protein (protein A, G, A/G or L) and may be economical as compared to the existing method of using a low molecular compound or protein A.

In still another aspect, the present invention is directed to an immunosensor in which rabbit or mouse immunoglobulin G is immobilized onto a solid substrate surface-treated with the repebody according to the present invention, using the repebody as a mediator.

In still another aspect, the present invention is directed to a method of detecting a substance having binding affinity for rabbit or mouse immunoglobulin G by use of the repebody of the present invention, the method comprising the steps of: (a) treating the above-described immunosensor with a sample containing the substance having binding affinity for rabbit or mouse immunoglobulin G; and (b) determining whether the substance would bind to the immunosensor.

In the present invention, the immunosensor may be obtained by treating the surface of a solid substrate with the repebody of the present invention, which binds specifically to the Fc region of immunoglobulin G, and then immobilizing an immunoglobulin G to be detected on the surface of the solid substrate. Determination of binding based on an antigen-antibody reaction by use of the immunosensor may vary depending on the kind of solid substrate. For example, when the solid substrate is composed of magnetic fine particles, the determination may be performed by a PAGE method after boiling the magnetic fine particles themselves in a buffer. In addition, when the solid substrate is composed of a glass plate, the determination may be performed by measuring fluorescence after treating the repebody with fluorescence-labeled immunoglobulin G. Furthermore, after the repebody is treated with an enzyme-immunoglobulin G conjugate, the binding therebetween may be detected by a visual detection method of observing color development by an enzymatic reaction, a spectrometric detection method of measuring a change in the absorbance of reflected light or transmitted light, or an electrochemical method of measuring an electric current or potential generated indirectly by an antigen-antibody reaction product.

In still another aspect, the present invention is directed to a composition for ELISA of mouse or rabbit immunoglobulin G, the composition comprising the repebody according to the present invention.

In general, compositions for ELISA are used for the detection or quantitative analysis of a target substance by an enzyme-linked antibody. Commercially available compositions for ELISA are generally prepared as compositions for ELISA in order to increase sensitivity and specificity. The composition for sandwich ELISA comprises two different antibodies capable of binding to a target substance. Among the two different antibodies, one antibody is bound to an immobilization substrate, and the other antibody is conjugated to an enzyme and used to perform a color development reaction.

The composition for sandwich ELISA is used as follows. A sample is added to an immobilization substrate having an antibody bound thereto, and an antigen contained in the sample is conjugated to the antibody bound to the substrate, thereby forming a substrate-antibody-antigen complex. Next, another antibody having conjugated thereto an enzyme for performing a color development reaction is added to the substrate and reacted with the complex, thereby forming a substrate-antibody-antigen-antibody-enzyme complex. Then, a substrate that develops color by a substrate is added to and reacted with the complex, and whether the substrate would develop color is examined or the level of color development is measured, thereby determining the presence or absence of a target antigen (target substance) in the sample or the amount of the antigen. If the target antigen is not present in the sample, a substrate-antibody-antigen-antibody-enzyme complex will not be formed, and thus a color development reaction will not occur even when the substrate is added.

A conventional composition for ELISA may comprise a repebody having HRP conjugated directly thereto. This is because if HRP having a size of about 44 kDa is conjugated directly to an antibody having a size of 100 to 200 kDa, the structure of the antibody will be changed due to the HRP and the antibody cannot perform its normal function. Thus, a conventional composition for ELISA is prepared to comprise either an HRP-conjugated secondary antibody or an antibody having HRP conjugated indirectly thereto by a biotin-streptavidin linker. For this reason, it has the disadvantage of time-consuming and cost-ineffective.

On the contrary, the composition for ELISA according to the present invention may comprise a repebody conjugated directly to HRP. This is because the binding affinity of the repebody, which has a size of about 29 kDa, for a target substance, is not influenced even when HRP having a relatively large size of 44 kDa is conjugated to the repebody. Thus, the composition for ELISA according to the present invention has excellent specificity and sensitivity, and is conveniently prepared because it comprises the repebody having HRP conjugated directly thereto.

In still another aspect, the present invention is directed to a composition for Western blotting of mouse or rabbit immunoglobulin G, the composition comprising the repebody according to the present invention.

In the present invention, Western blotting is a technique that detects any specific protein in a mixture of various proteins. In this technique, when protein extracted from cells or tissue is mixed with a sample buffer and placed and electrophoresed on a molecular sieve made of acrylamide, the substance sodium dodecylsulfate (SDS)-PAGE contained in a sample buffer negatively charges the protein which then moves toward positive charges. At this time, the molecular sieve interferes with the movement of the protein such that small molecules move rapidly and large molecules move slowly, thereby forming bands having different sizes. When a membrane is placed on a gel divided by size and electricity is added thereto, the protein is transferred to the membrane in a separated state. At this time, primary antibody against a specific protein to be detected is allowed to be bind to the protein, and secondary antibody specific for the primary antibody is allowed to bind. Then, a reaction indicated by color development or fluorescence is imaged with X-rays. In general, an antibody against immunoglobulin G is mainly used as the secondary antibody. However, when the repebody according to the present invention is used instead of the antibody, it may have advantages in that it has excellent sensitivity and specificity and is conveniently produced.

In still another aspect, the present invention is directed to a composition for immunohistochemical staining of mouse or rabbit immunoglobulin G, the composition comprising the repebody of the present invention, which has a fluorescent substance conjugated thereto.

In general, immunochemical staining is performed as follows. A primary antibody against a specific antigen is reacted and attached, after which a secondary antibody having an enzyme attached directly thereto is attached and a substrate for the enzyme is reacted to develop color. Alternatively, a biotin-conjugated secondary antibody is reacted, and then a reagent having an enzyme attached to avidin having the property of strongly binding to biotin is reacted (ABC method), after which a substrate for the enzyme is reacted to develop color. Next, the presence of the original antigen is observed under a microscope. In this method, the final level of color development varies depending on various factors that determine the reactivity of the enzyme. In particular, in the ABC method that is most frequently used, multi-step staining is performed, and for this reason, the originally present antigen is amplified in multiple steps and develops vivid color. However, since these steps all influence the final level of color development, it is not sufficient to achieve the original purpose of quantitatively determining the amount of an antigen in tissue. In comparison with this, the composition for immunohistochemical staining, which comprises the repebody according to the present invention, uses the repebody, which binds specifically to immunoglobulin G and has a fluorescent substance conjugated thereto, instead of a secondary antibody, and thus it has high sensitivity and accuracy and makes it possible to perform immunohistochemical staining in a sample manner.

In the present invention, the fluorescent substance may be a fluorescent dye, a tetracystein motif, a fluorescent protein, a fluorescent nanoparticle or a quantum dot, but is not limited thereto.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1

Construction of Libraries for Screening Repebodies, Which Bind Specifically to Mouse and Rabbit Immunoglobulin G, by Phage Display To screen repebodies that bind specifically to rabbit immunoglobulin G, phage display was performed using a phage library previously constructed according to a prior art patent document (Korean Patent Application No. 10-2012-0019927) (FIG. 1). To screen repebodies that bind specifically to mouse immunoglobulin G, six amino residues (240, 241, 242, 243, 244 and 255) located in the carboxyl terminus were selected based on the polypeptide sequence of a repebody, which was developed in a prior art patent document (Korean Patent Application No. 10-2013-0081009) and binds to human immunoglobulin G (FIG. 2). FIGS. 1 and 2 are schematic views showing overall structures that represent amino acid residues used to construct random libraries.

Mutagenic primers for constructing libraries were synthesized such that the selected amino acid residues would be substituted with NNK degenerate codons.

Next, using the primers, overlap PCR for two modules was performed, thereby obtaining DNA libraries. The DNA libraries were inserted into the phagemid pBEL118M of SEQ ID NO: 2 described in the prior art patent document (Korean Patent Application No. 10-2012-0019927) of the present inventors, thereby obtaining phagemid libraries.

The obtained libraries were introduced into *E. coli* XL1-Blue by electroporation, thereby obtaining transformant libraries having a diversity of $1.0 \times 10^8$.

Example 2

Screening of Polypeptides, Which Binds to Mouse and Rabbit Immunoglobulins G, by Panning of Repebody Libraries Using the libraries constructed in Example 1, polypeptides capable of binding to mouse and rabbit immunoglobulins G were screened and purified. To screen candidates capable of binding to mouse or rabbit immunoglobulin G, mouse or rabbit immunoglobulin G was added to an immuno-tube at a concentration of 30 µg/ml and coated on the tube at 4° C. for 12 hours. The coated immune-tube was washed once with PBS and blocked with PBS solution (TPBSA) containing 1% BSA and 0.05% Tween 20 at 4° C. for 2 hours. Thereafter, the purified phages were added to the coated immune-tube at a concentration of $10^{12}$ cfu/ml and incubated at room temperature for 2 hours. After completion of the incubation, the immuno-tube was washed five times with PBS solution (TPBS) containing 0.05% Tween 20 for a total of 2 minutes. Finally, 1 ml of 0.2 M glycine-HCl (pH 2.2) was added to the immuno-tube and incubated at room temperature for 12 minutes, thereby eluting phages having displayed on the surface thereof repebody candidates capable of mouse or rabbit immunoglobulin G. The eluate was neutralized by addition of 60 µl of 1.0 M Tris-HCl (pH 9.0), and added to 10 ml of *E. coli* XL1-Blue (host cell) solution ($OD_{600}=0.5$), and then plated on a 2×YT plate. This biopanning round was repeated five times in the same manner.

As a result, it was shown that phages that bind specifically to mouse and rabbit immunoglobulins G were enriched through each biopanning round. This result suggests that phages that bind to mouse and rabbit immunoglobulins G specifically increased.

Example 3

Examination of the Specific Binding Affinities of Selected Repebodies for Mouse and Rabbit Immunoglobulins G and Sequencing of the Repebodies The phages screened through the method of Example 2 were subjected to ELISA using 96-well plates coated with mouse and rabbit immunoglobulins G and BSA. To screen repebodies that bind to rabbit immunoglobulin G, 41 repebody candidates for which the absorbance ($OD_{450}$) of rabbit immunoglobulin G was at least 10 times higher than that of BSA were selected, and the amino acid sequences of these selected repebody candidates were analyzed. As a result, one repebody having a sequence common to all the selected phages was found (SEQ ID NO: 3).

To screen repebodies that bind to mouse immunoglobulin G, 4 repebody candidates for which the absorbance ($OD_{450}$) of mouse immunoglobulin G was at least 4 times higher than that of BSA were selected, and the amino acid sequences of these selected repebody candidates were analyzed, after which clones having the same amino acid sequence were excluded. As a result, a total of three repebody sequences were found in the selected phages (SEQ ID NOs: 4 to 6).

Example 4

Module-Based Affinity Amplification Method for Increasing Binding Affinities of Repebodies For use in various immunoassays, repebodies need to be improved to have a binding affinity similar to the binding affinities of conventional secondary immunoglobulin G for primary immunoglobulin G. Thus, to ensure repebodies having increased binding affinity, the module-based affinity amplification technology disclosed in a prior art patent document (Korean Patent Application No. 10-2012-0019927) was used. First, based on the polynucleotide sequence encoding the polypeptide of the E2 repebody that binds to rabbit immunoglobulin G, selected in Example 3, modules (LRRVS and LRRVE) adjacent to the first library were selected, and six residues in the concave region were mutated in the same manner as described in Example 2 of the prior art patent document. Then, a total of five panning rounds were performed to select a total of six repebody clones having increased binding affinities. The dissociation constants of the selected repebody clones were measured by ITC, and as a result, E2 repebody having the highest binding affinity of 74 nM was finally selected (FIG. 3).

Figure 4:
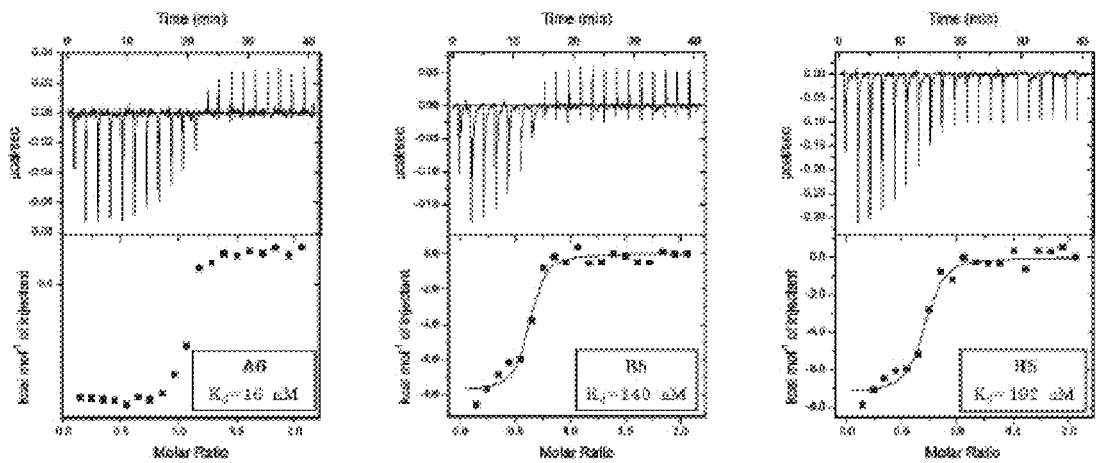
FIG. 4 shows the results of isothermal titration calorimetry (ITC) performed to measure the binding affinities of repebody clones finally selected after performing phage display biopanning for mouse immunoglobulins G by use of the phage libraries constructed in the present invention.

Next, from a total of three repebody clones that bind to mouse immunoglobulin G, selected in Example 3, two modules (LRR1 and LRRV2) in the amino terminus of the H12 repebody were selected based on the polynucleotide sequence encoding the polypeptide of the H12 repebody, and six residues in the concave region were mutated in the same manner as described in Example 2 of the prior art patent document. Then, a total of five panning rounds were performed to select a total of three repebody clones having increased binding affinities. The dissociation constants of the selected repebody clones were measured by ITC, and as a result, it was shown that A6 repebody had the highest binding affinity of 16 nM (FIG. 4).

Example 5

Analysis of the Potential of Selected Repebodies to Replace Conventional Secondary Immunoglobulin G Using the two repebodies selected in Example 4 together with the F4 repebody that binds to human immunoglobulin G, disclosed in a prior art patent document (Korean Patent Application No. 10-2013-0081009), the potential of these repebodies to replace conventional immunoglobulins G that bind to human, mouse and rabbit immunoglobulins G was analyzed. To this end, analysis was performed of whether the detection of non-specific signals and cross-reactivity, which are the disadvantages of conventional secondary immunoglobulins G, would occur. Each of human, mouse and rabbit immunoglobulins G was coated on 96-well plates at a concentration of 30 µg/ml and the plates were kept at 4° C. for 10 hours. Next, the plates were washed once with PBS solution (TPBS) containing 0.05% Tween 20. NHS-fluorescein (NHS-FITC), a fluorescent marker absorbs energy at 485 nm and emits light at 510 nm, was conjugated to the primary amine group of each of the repebodies, thereby constructing repebody-fluorescent marker conjugates (repebody-FITC). Then, the coated 96-well plates were treated with the conjugates at the same concentration of 10 µg/ml. After 1 hour of incubation at room temperature, the plates were washed three times with TPBS.

Figure 5:
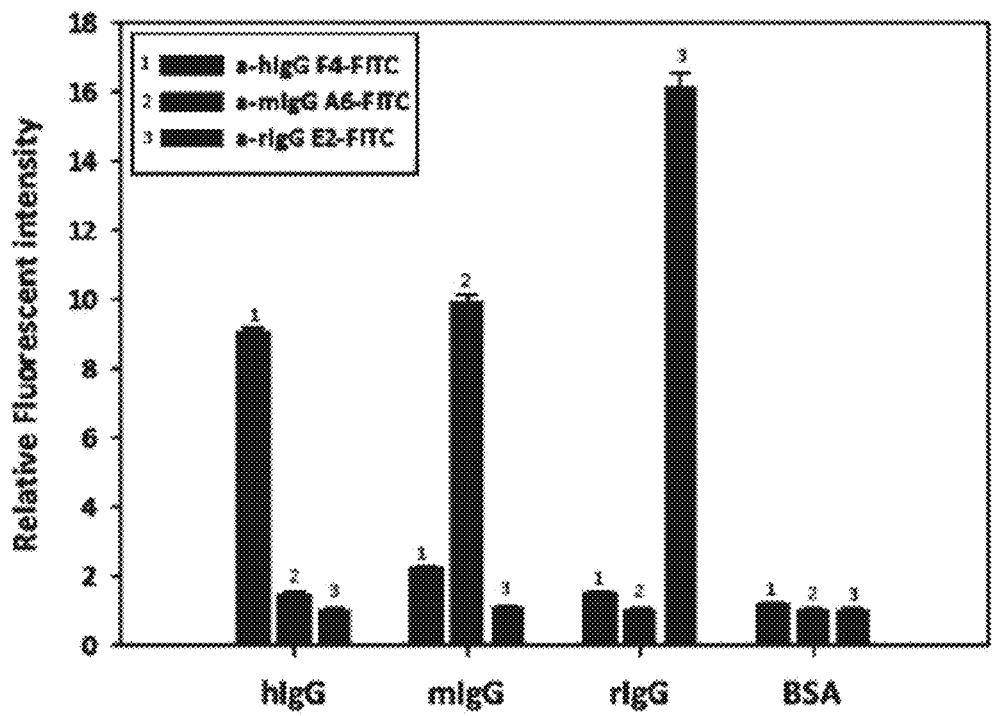
FIG. 5 shows the results of ELISA fluorescence assay performed to determine whether repebody clones having the high binding affinities for human, mouse and rabbit immunoglobulins G would bind specifically to the immunoglobulins G. The specificity of a repebody that binds specifically to human immunoglobulin G, developed by the present inventors as disclosed in a prior art patent document (Korean Patent Application No. 10-2013-0081009) was also analyzed. It could be seen that all the clones did bind specifically to their respective immunoglobulins G without binding to BSA.

The level of light emission from each of the repebody-fluorescent marker conjugates was measured, and as a result, it was found that F4-FITC, A6-FITC and E2-FITC showed fluorescence only in human immunoglobulin G, mouse immunoglobulin G and rabbit immunoglobulin G, respectively (FIG. 5). This indicates that the selected repebodies overcome the detection limit caused by the non-specific reaction and cross-reactivity of conventional secondary immunoglobulins G, and bind specifically to the immunoglobulin G of each animal species, suggesting that these repebodies have the potential to replace conventional secondary immunoglobulins G.

Example 6

Verification of the Utility of Selected Repebodies in ELISA Assay

The selected repebodies were actually applied to ELISA, and an experiment was performed to compare the target protein detection ability between treatment with the repebodies and treatment with conventional secondary immunoglobulins G under the same conditions. An experiment that conjugated an enzyme as a detection marker to the repebodies was performed, thereby obtaining repebody-enzyme conjugates (repebody-HRP) in a yield of 90% or higher. For ELISA assay, each of human, mouse and rabbit immunoglobulins G was coated on 96-well plates at various concentrations of 0 to 2 µg/ml and the plates were kept at 4° C. for 10 hours. Next, the plates were washed once with PBS solution (TPBS) containing 0.05% Tween 20. The coated plates were treated with 0.2 µg/ml of each of F4-HRP, A6-HRP, E2-HRP and conventional secondary immunoglobulin G-HRP. After 1 hour of incubation at room temperature, the plates were washed three times with TPBS, and then treated with tetramethylbenzidine (TMB), a substrate for HRP, for 20 minutes. The plates were treated with sulfuric acid to stop the reaction, and the absorbance at a wavelength of 450 nm was measured.

Figure 6:
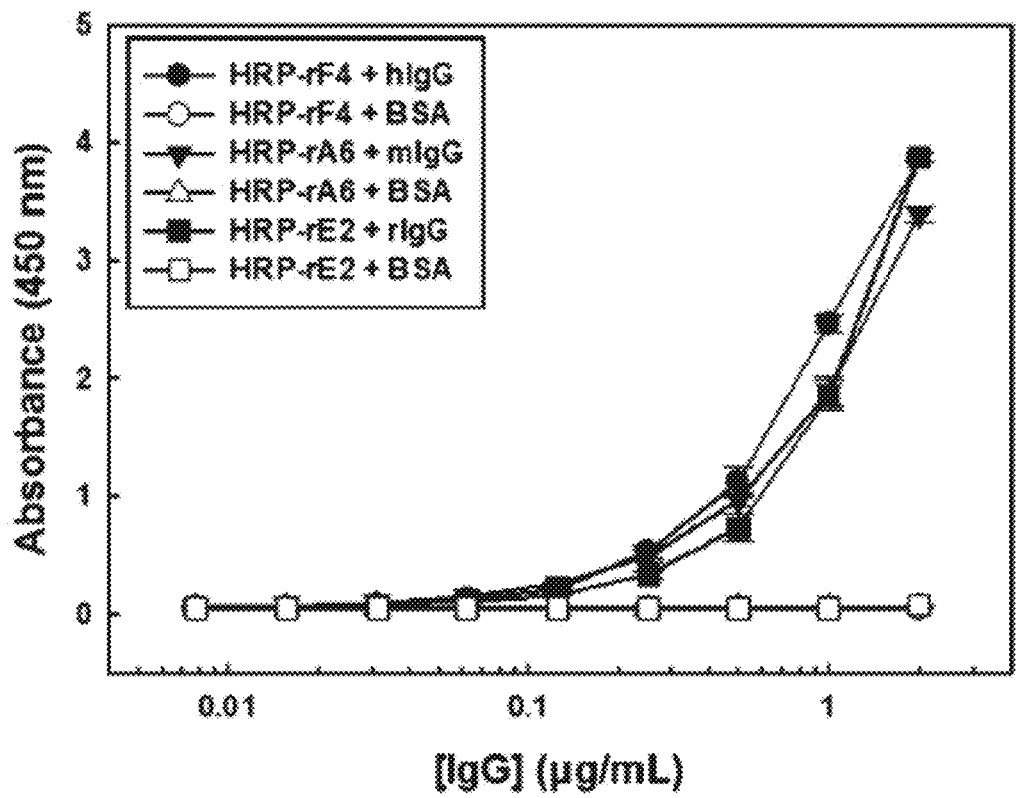
FIG. 6 shows the results of ELISA performed to compare the target protein detection ability between conventional secondary immunoglobulin G-enzyme conjugates and repebody-enzyme conjugates. When various concentrations of immunoglobulin G were treated with each of conventional secondary immunoglobulin G-enzyme conjugates and the same mass of repebody-enzyme conjugates, it could be seen that the ability of the repebody-enzyme conjugates to detect immunoglobulin G was equal to or better than the conventional secondary immunoglobulin G-enzyme conjugates.

As a result, it was shown that the repebodies detected 50 ng/ml or more of human, mouse and rabbit immunoglobulins G, like to the conventional secondary immunoglobulin G (FIG. 6). This suggests that these repebodies have an excellent ability to detect a concentration which is at least 50 times lower than 0.1 to 1 µg/ml of primary immunoglobulin, which is actually used.

Example 7

Verification of the Utility of Selected Repebodies in Western Blot Assay

Figure 7:
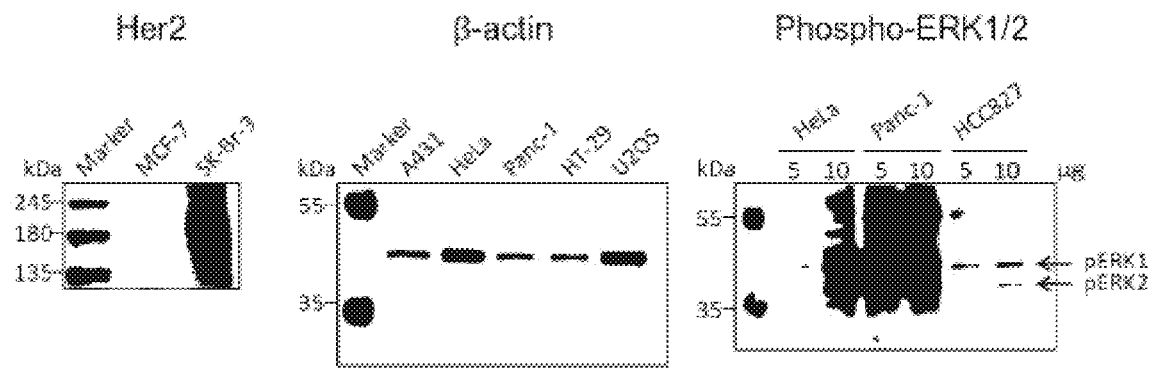
FIG. 7 shows the results of Western blot assay performed to examine the ability of repebody-enzyme conjugates to detect their target proteins. The target proteins are human epidermal growth factor receptor 2 (HER2), intracellular filament (β-actin) and phosphorylated kinase (phospho-ERK1/2), which are overexpressed in breast cancer cells. When various types of animal cells were lysed, and then the cell lysates containing various proteins were treated with primary immunoglobulin G that recognizes only a target protein, followed by treatment with repebody-enzyme conjugates that bind to primary immunoglobulin G, it could be seen that only the target protein was specifically detected.

The selected repebodies were actually applied to Western blotting, and an experiment was performed to evaluate the ability to specifically detect only a target protein in complex cell lysates. First, the detection ability of F4-HRP that binds to human immunoglobulin G was evaluated. Human breast cancer cells (SK-Br-3 and MCF-7) were lysed. To detect HER2 among a variety of complex proteins contained in the lysate, 20 µg of the cell lysate was subjected to SDS-PAGE to separate proteins by size, and was treated with 1 µg/ml of herceptin, a human immunoglobulin G that binds specifically to HER2. After 1 hour of incubation at room temperature, the cell lysate was washed three times with TPBS. Next, the cell lysate was treated with 2 µg/ml of F4-HRP, incubated at room temperature for 1 hour, and then washed three times with TPBS. The cell lysate was treated with a substrate to detect a chemiluminescent signal, and as a result, it was shown that the F4-HRP did bind specifically to HER2 and a signal was detected (FIG. 7).

Next, the detection ability of A6-HRP that binds to mouse immunoglobulin G was evaluated. To detect β-actin in cell lysates obtained from various types of animal cancer cells (A431, HeLa, Panc-1, HT-29, and U2OS), 20 µg of each cell lysate was subjected to SDS-PAGE to separate proteins by size, and was treated with 0.2 µg/ml of anti-β-actin mouse IgG, a primary mouse immunoglobulin G that binds specifically to β-actin. After 1 hour of incubation at room temperature, the cell lysate was washed three times with TPBS. Next, then cell lysate was treated with 0.5 µg/ml of A6-HRP, incubated at room temperature for 1 hour, and then washed three times with TPBS. The cell lysate was treated with a substrate to detect a chemiluminescent signal, and as a result, it was shown that the A6-HRP did bind specifically to β-actin and a signal was detected (FIG. 7).

Finally, the detection ability of E2-HRP that binds to rabbit immunoglobulin G was evaluated. Next, the detection ability of A6-HRP that binds to mouse immunoglobulin G was evaluated. To detect phosphorylated kinase (phospho-ERK1/2) in cell lysates obtained from various types of animal cancer cells (HeLa, Panc-1, HCC827), 20 µg of each cell lysate was subjected to SDS-PAGE to separate proteins by size, and was treated with 1 µg/ml of anti-phospho-ERK1/2 rabbit IgG, a primary rabbit immunoglobulin G that binds specifically to phospho-ERK1/2. After 1 hour of incubation at room temperature, the cell lysate was washed three times with TPBS. Next, then cell lysate was treated with 2 µg/ml of E2-HRP, incubated at room temperature for 1 hour, and then washed three times with TPBS. The cell lysate was treated with a substrate to detect a chemiluminescent signal, and as a result, it was shown that the E2-HRP did bind specifically to phospho-ERK1/2 and a signal was detected (FIG. 7).

Example 8

Verification of the Utility of Selected Repebodies in Immunocytochemistry

Figure 8:
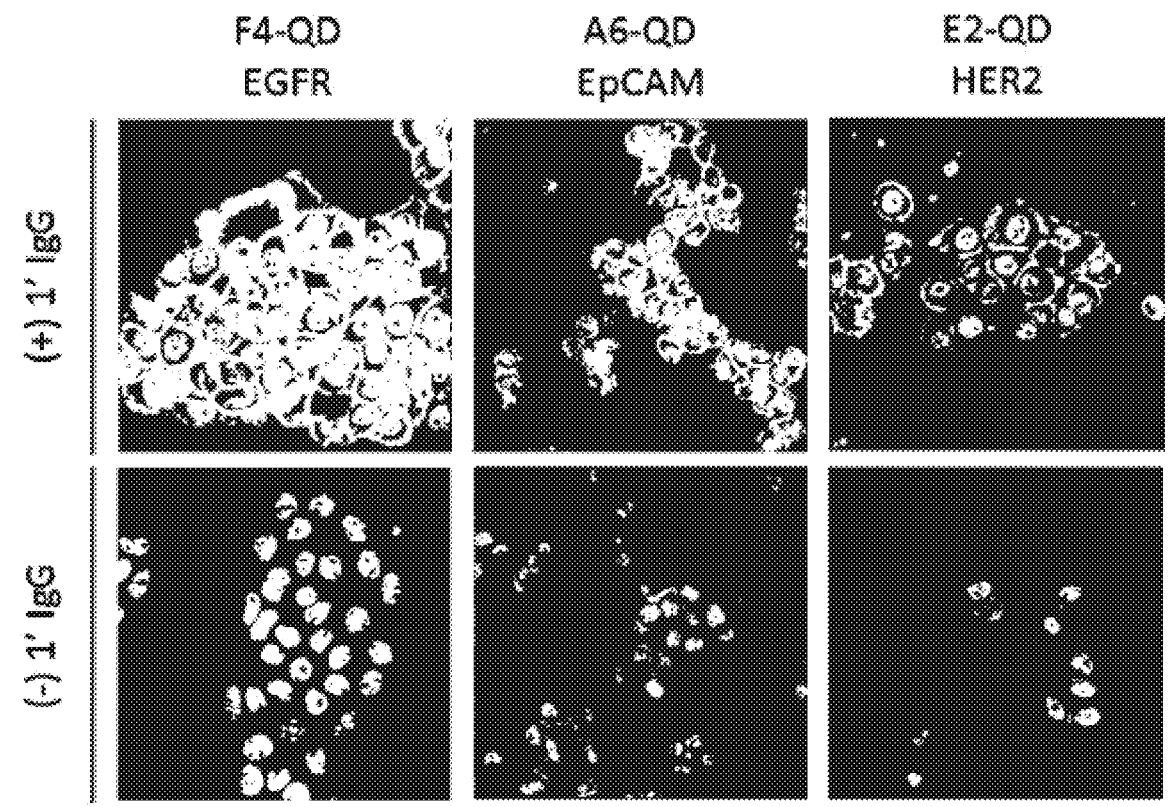
FIG. 8 shows the results of immunocytochemistry performed to detect target proteins by repebody-quantum dot conjugates and to image cells. The target proteins are epidermal growth factor receptor (EGFR), epithelial cell adhesion molecule (EpCAM) and HER2, which are overexpressed in cancer cells. After treatment with primary immunoglobulin G that binds specifically to a target protein, followed by detection of the fluorescent signals of repebody-quantum dot conjugates, it could be seen that the fluorescent signals were detected only in the groups treated with primary immunoglobulin G.

FIG. 8 shows the results of immunocytochemistry performed to detect target proteins by repebody-quantum dot conjugates (repebody-QD) and to image cells. The target proteins are epidermal growth factor receptor (EGFR), epithelial cell adhesion molecule (EpCAM) and HER2, which are overexpressed in cancer cells. To construct F4-QD, A6-QD and E2-QD, an NHS/EDC linker was introduced to link the primary amine group of each repebody to quantum dots (QD) having an exposed carboxyl group, thereby constructing conjugates in a very high yield of 99%. As the QD, QD emitting green light at a wavelength of 525 nm were used.

The animal cells present in cell culture medium (RPMI-1640) were incubated in an 8-well cell culture chamber for 48 hours and attached to the surface. Next, the cells were treated with 2 μg of each of cetuximab, anti-EpCAM mouse IgG and anti-HER2 rabbit IgG, which are primary immunoglobulins G that bind specifically to target proteins. The cells were incubated for 1 hour at 4° C. Next, the cells were washed twice with DPBS, treated with 20 nM of each of F4-QD, A6-QD and E2-QD, and then incubated at 4° C. for 1 hour. Thereafter, the cells were treated twice with DPBS, and then DAPI solution was dropped on the cells for nucleus staining and slide glass mounting. The fluorescent signals of the repebody-QD were detected using a confocal microscope, and as a result, it was shown that the fluorescent signals were detected only in the groups treated with the primary immunoglobulins G (FIG. 8).

The results of the experiments on the application of the repebodies to immunoassays as described in Examples 5 to 8 above indicate that the repebodies overcome the disadvantages of conventional secondary immunoglobulins G, including the detection limit caused by non-specific reaction and cross-reactivity, as well as high production costs, bind specifically to their target proteins, and show significantly low cross-reactivity. In addition, these repebodies can be produced in *E. coli* in large amounts, and in this respect, they are novel and innovative proteins that can be produced at costs equal to ¹/₁₀ of the production costs of conventional expensive secondary immunoglobulins G. When these repebodies were applied to various immunoassays, they showed a sufficient ability to detect their target proteins, suggesting that these repebodies can be used in the manufacture of immunosensors/immunochips, target-directed DDS carriers for drug delivery, and biological drugs.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The novel peptide according to the present invention binds specifically to mouse or rabbit immunoglobulin G, can replace conventional expensive secondary immunoglobulin G, and can be used in various biological immunoassays. In addition, a conjugate of the polypeptide of the present invention and immunoglobulin G is useful for fabrication of various immunosensors/immunochips and for drug screening.

The invention claimed is:

1. A repebody comprising any one of the amino acid sequences represented by SEQ ID NOS: 4 to 6 and 13 to 15, the repebody binding selectively to mouse immunoglobulin G.

2. A polynucleotide encoding the repebody of claim 1.

3. A recombinant vector comprising the polynucleotide of claim 2.

4. A recombinant microorganism into which the polynucleotide of claim 2 or a recombinant vector comprising said polynucleotide is introduced.

5. A method for producing the repebody of claim 1, wherein the method comprises:
   (i) introducing into a host microorganism (a) a polynucleotide encoding a repebody comprising any one of the amino acid sequences represented by SEQ ID NOS: 4 to 6 and 13 to 15, the repebody binding selectively to mouse immunoglobulin G, or (b) a recombinant vector comprising said polynucleotide, to thereby produce a recombinant microorganism;
   (ii) expressing the repebody by culturing the recombinant microorganism; and
   (iii) recovering the expressed repebody.

6. A method for purifying a mouse immunoglobulin G antibody, wherein the method comprises the steps of:
   (i) injecting a mixture comprising a mouse immunoglobulin G antibody into a column into which the repebody of claim 1 is adsorbed; and
   (ii) eluting the antibody attached to the column of step (i).

7. A method for immobilizing mouse immunoglobulin G, wherein the method comprises the steps of:
   (i) treating a surface of a solid substrate by attaching the repebody of claim 1 onto the solid substrate; and
   (ii) binding mouse immunoglobulin G to the surface-treated solid substrate.

8. An immunosensor having a solid substrate surface-treated with the repebody of claim 1, such that the repebody is attached to the solid substrate, and wherein mouse immunoglobulin G is immobilized to the solid substrate by binding to the repebody.

9. A method of detecting a substance having binding affinity for mouse immunoglobulin G, the method comprising the steps of:
   (a) treating the immunosensor of claim 8 with a sample containing the substance having binding affinity for mouse immunoglobulin G; and
   (b) determining whether the substance would bind to the immunosensor.

10. A composition for ELISA of mouse immunoglobulin G, the composition comprising the repebody of claim 1.

11. A composition for Western blotting of mouse immunoglobulin G, the composition comprising the repebody of claim 1.

12. A composition for immunohistochemical staining of mouse immunoglobulin G, the composition comprising the repebody of claim 1, which has a fluorescent substance conjugated thereto.

13. The composition of claim 12, wherein the fluorescent substance is a fluorescent dye, a tetracystein motif, a fluorescent protein, a fluorescent nanoparticle, or a quantum dot.

* * * * *

UNITED STATES PATENT AND TRADEMARK OFFICE
CERTIFICATE OF CORRECTION

PATENT NO. : 10,995,153 B2
APPLICATION NO. : 16/074530
DATED : May 4, 2021
INVENTOR(S) : Hak-Sung Kim et al.

It is certified that error appears in the above-identified patent and that said Letters Patent is hereby corrected as shown below:

In the Specification

Column 14, Line 48, "LRRVS" should be -- LRRV5 --.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 15

<210> SEQ ID NO 1
<211> LENGTH: 798
<212> TYPE: DNA
<213> ORGANISM: Artificial Sequence
<220> FEATURE:
<223> OTHER INFORMATION: Repebody-Library1
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (145)..(146)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (214)..(215)
<223> OTHER INFORMATION: n is a, c, g, or t
```

-continued

<400> SEQUENCE: 1

| | | | | | |
|---|---|---|---|---|---|
| gaaaccatta | ccgtgagcac | cccgatcaaa | cagatttttc | cggatgacgc | gttcgccgaa | 60 |
| acgatcaaag | caaacctgaa | gaaaagagc | gttaccgatg | ctgtcacgca | aaatgaactg | 120 |
| aacagtattg | accagatcnn | kgcgnnknnk | tccgatatca | aatcagtgca | aggcattcag | 180 |
| tatctgccga | atgttcgtta | cctgnnkctg | nnknnkaaca | aactgcatga | catctcggca | 240 |
| ctgaaagaac | tgaccaatct | gacgtatctg | attctgaccg | gtaaccaact | gcagagcctg | 300 |
| ccgaatggcg | tctttgataa | actgacgaac | ctgaaagaac | tggtgctggt | tgaaaatcaa | 360 |
| ctgcagtctc | tgccggacgg | tgtcttcgat | aaactgacca | acctgacgta | cctgaatctg | 420 |
| gctcacaacc | aactgcagag | tctgccgaaa | ggcgtgtttg | acaaactgac | caatctgacg | 480 |
| gaactggatc | tgtcctataa | ccaactgcag | tcactgccgg | aaggtgtttt | cgacaaactg | 540 |
| acccagctga | aagatctgcg | cctgtaccag | aatcagctga | atcggtccc | ggacggcgtg | 600 |
| tttgatcgtc | tgaccagcct | gcagtatatc | tggctgcatg | ataaccgtg | ggattgcacc | 660 |
| tgtccgggta | ttcgctacct | gtctgaatgg | atcaataaac | acagtggcgt | tgtccgtaac | 720 |
| tccgcgggtt | cagttgcccc | ggattcggcg | aaatgctccg | gcagcggtaa | accggtgcgt | 780 |
| agcattattt | gcccgacc | | | | | 798 |

<210> SEQ ID NO 2
<211> LENGTH: 798
<212> TYPE: DNA
<213> ORGANISM: Artificial Sequence
<220> FEATURE:
<223> OTHER INFORMATION: Repebody-Library2
<220> FEATURE:
<221> NAME/KEY: misc_feature
<222> LOCATION: (718)..(719)
<223> OTHER INFORMATION: n is a, c, g, or t
<220> FEATURE:
<221> NAME/KEY: misc_feature
<222> LOCATION: (721)..(722)
<223> OTHER INFORMATION: n is a, c, g, or t
<220> FEATURE:
<221> NAME/KEY: misc_feature
<222> LOCATION: (724)..(725)
<223> OTHER INFORMATION: n is a, c, g, or t
<220> FEATURE:
<221> NAME/KEY: misc_feature
<222> LOCATION: (727)..(728)
<223> OTHER INFORMATION: n is a, c, g, or t
<220> FEATURE:
<221> NAME/KEY: misc_feature
<222> LOCATION: (730)..(731)
<223> OTHER INFORMATION: n is a, c, g, or t
<220> FEATURE:
<221> NAME/KEY: misc_feature
<222> LOCATION: (733)..(734)
<223> OTHER INFORMATION: n is a, c, g, or t

<400> SEQUENCE: 2

| | | | | | |
|---|---|---|---|---|---|
| gaaaccatta | ccgtgagcac | cccgatcaaa | cagatttttc | cggatgacgc | gttcgccgaa | 60 |
| acgatcaaag | caaacctgaa | gaaaagagc | gttaccgatg | ctgtcacgca | aaatgaactg | 120 |
| aacagtattg | accagatcat | tgcgaataac | tccgatatca | aatcagtgca | aggcattcag | 180 |
| tatctgccga | atgttcgtta | cctggccctg | ggtggcaaca | aactgcatga | catctcggca | 240 |
| ctgaaagaac | tgaccaatct | gacgtatctg | attctgaccg | gtaaccaact | gcagagcctg | 300 |
| ccgaatggcg | tctttgataa | actgacgaac | ctgaaagaac | tggtgctggt | tgaaaatcaa | 360 |
| ctgcagtctc | tgccggacgg | tgtcttcgat | aaactgacca | acctgacgta | cctgaatctg | 420 |
| gctcacaacc | aactgcagag | tctgccgaaa | ggcgtgtttg | acaaactgac | caatctgacg | 480 |

```
gaactggatc tgtcctataa ccaactgcag tcactgccgg aaggtgtttt cgacaaactg    540
acccagctga agatctgcg cctgtaccag aatcagctga atcggtccc ggacggcgtg      600 tttgatcgtc tgaccagcct gcagtatatc tggctgcatg ataacccgtg ggattgcacc    660
tgtccgggta ttcgctacct gtctgaatgg atcaataaac acagtggcgt tgtccgtnns    720
nnsnnsnnsn nsnnsgcccc ggattcggcg aaatgctccg gcagcggtaa accggtgcgt    780
agcattattt gcccgacc                                                  798
```

<210> SEQ ID NO 3
<211> LENGTH: 266
<212> TYPE: PRT
<213> ORGANISM: Artificial Sequence
<220> FEATURE:
<223> OTHER INFORMATION: Repebody-E7

<400> SEQUENCE: 3

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Met Ala
        35                  40                  45

Met Gln Ser Asp Ile Lys Ser Val Gln Gly Ile Gln Tyr Leu Pro Asn
    50                  55                  60

Val Arg Tyr Leu Phe Leu Phe Gln Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265
```

<210> SEQ ID NO 4
<211> LENGTH: 266
<212> TYPE: PRT
<213> ORGANISM: Artificial Sequence
<220> FEATURE:
<223> OTHER INFORMATION: Repebody-rME9

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Glu Leu Lys Trp Asn Gln
                85                  90                  95

Leu Gln Ile Leu Pro Asn Gly Val Phe Asp Lys Leu Thr Asn Leu Lys
            100                 105                 110

Glu Leu Val Leu Asn Ser Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Leu
225                 230                 235                 240

Phe Thr Trp Ser Leu Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 5
<211> LENGTH: 266
<212> TYPE: PRT
<213> ORGANISM: Artificial Sequence
<220> FEATURE:
<223> OTHER INFORMATION: Repebody-rMF1

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

```
Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Glu Leu Lys Trp Asn Gln
                 85                  90                  95

Leu Gln Ile Leu Pro Asn Gly Val Phe Asp Lys Leu Thr Asn Leu Lys
            100                 105                 110

Glu Leu Val Leu Asn Ser Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Leu
225                 230                 235                 240

His Ser Phe Pro Met Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 6
<211> LENGTH: 266
<212> TYPE: PRT
<213> ORGANISM: Artificial Sequence
<220> FEATURE:
<223> OTHER INFORMATION: Repebody-H12

<400> SEQUENCE: 6

Glu Thr Ile Thr Val Ser Thr Pro Ile Lys Gln Ile Phe Pro Asp Asp
  1               5                  10                  15

Ala Phe Ala Glu Thr Ile Lys Ala Asn Leu Lys Lys Lys Ser Val Thr
                 20                  25                  30

Asp Ala Val Thr Gln Asn Glu Leu Asn Ser Ile Asp Gln Ile Ile Ala
             35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Glu Leu Lys Trp Asn Gln
                 85                  90                  95

Leu Gln Ile Leu Pro Asn Gly Val Phe Asp Lys Leu Thr Asn Leu Lys
            100                 105                 110

Glu Leu Val Leu Asn Ser Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Asp Gly Val Phe Asp Lys Leu Thr Asn Leu Thr
145                 150                 155                 160
```

-continued

```
Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Leu
225                 230                 235                 240

Met Ser Ser Leu Met Ala Pro Asp Ser Ala Lys Cys Ser Gly Ser Gly
                245                 250                 255

Lys Pro Val Arg Ser Ile Ile Cys Pro Thr
                260                 265
```

<210> SEQ ID NO 7
<211> LENGTH: 264
<212> TYPE: PRT
<213> ORGANISM: Artificial Sequence
<220> FEATURE:
<223> OTHER INFORMATION: Repebody-C9

<400> SEQUENCE: 7

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Gln Leu Thr Pro Asn Gln
                85                  90                  95

Ser Leu Pro Asn Gly Val Phe Asp Lys Leu Thr Asn Leu Lys Glu Leu
            100                 105                 110

Ile Leu Pro Leu Asn Gln Leu Gln Ser Leu Pro Asp Gly Val Phe Asp
        115                 120                 125

Lys Leu Thr Asn Leu Thr Tyr Leu Asn Leu Ala His Asn Gln Leu Gln
    130                 135                 140

Ser Leu Pro Lys Gly Val Phe Asp Lys Leu Thr Asn Leu Thr Glu Leu
145                 150                 155                 160

Asp Leu Thr Ala Asn Gln Leu Gln Ser Leu Pro Glu Gly Val Phe Asp
                165                 170                 175

Lys Leu Thr Gln Leu Lys Asp Leu Arg Leu Tyr Gln Asn Gln Leu Lys
            180                 185                 190

Ser Val Pro Asp Gly Val Phe Asp Arg Leu Thr Ser Leu Gln Tyr Ile
        195                 200                 205

Trp Leu His Asp Asn Pro Trp Asp Cys Thr Cys Pro Gly Ile Arg Tyr
    210                 215                 220

Leu Ser Glu Trp Ile Asn Lys His Ser Gly Val Val Arg Asn Ser Ala
225                 230                 235                 240
```

```
Gly Ser Val Ala Pro Asp Ser Ala Lys Cys Ser Gly Ser Gly Lys Pro
                245                 250                 255

Val Arg Ser Ile Ile Cys Pro Thr
            260
```

<210> SEQ ID NO 8
<211> LENGTH: 264
<212> TYPE: PRT
<213> ORGANISM: Artificial Sequence
<220> FEATURE:
<223> OTHER INFORMATION: Repebody-C10

<400> SEQUENCE: 8

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Gln Leu Thr Pro Asn Gln
                85                  90                  95

Ser Leu Pro Asn Gly Val Phe Asp Lys Arg Thr Asn Leu Lys Glu Leu
            100                 105                 110

Ile Leu Pro Leu Asn Gln Leu Gln Ser Leu Pro Asp Gly Val Phe Asp
        115                 120                 125

Lys Leu Thr Asn Leu Thr Tyr Leu Asn Leu Ala His Asn Gln Leu Gln
130                 135                 140

Ser Leu Pro Lys Gly Val Phe Asp Lys Leu Thr Asn Leu Thr Glu Leu
145                 150                 155                 160

Asp Leu Ser Tyr Asn Gln Leu Gln Ser Leu Pro Glu Gly Val Phe Asp
                165                 170                 175

Lys Leu Thr Gln Leu Lys Asp Leu Arg Leu Ile Phe Asn Gln Leu Lys
            180                 185                 190

Ser Val Pro Asp Gly Val Phe Asp Arg Leu Thr Ser Leu Gln Tyr Ile
        195                 200                 205

Trp Leu His Asp Asn Pro Trp Asp Cys Thr Cys Pro Gly Ile Arg Tyr
210                 215                 220

Leu Ser Glu Trp Ile Asn Lys His Ser Gly Val Val Arg Asn Ser Ala
225                 230                 235                 240

Gly Ser Val Ala Pro Asp Ser Ala Lys Cys Ser Gly Ser Gly Lys Pro
                245                 250                 255

Val Arg Ser Ile Ile Cys Pro Thr
            260
```

<210> SEQ ID NO 9
<211> LENGTH: 264
<212> TYPE: PRT
<213> ORGANISM: Artificial Sequence
<220> FEATURE:
<223> OTHER INFORMATION: Repebody-E2

<400> SEQUENCE: 9

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Gln Leu Thr Pro Asn Gln
                85                  90                  95

Ser Leu Pro Asn Gly Val Phe Asp Lys Leu Thr Asn Leu Lys Glu Leu
            100                 105                 110

Ile Leu Pro Leu Asn Gln Leu Gln Ser Leu Pro Asp Gly Val Phe Asp
        115                 120                 125

Lys Leu Thr Asn Leu Thr Tyr Leu Asn Leu Ala His Asn Gln Leu Gln
    130                 135                 140

Ser Leu Pro Lys Gly Val Phe Asp Lys Leu Thr Asn Leu Thr Glu Leu
145                 150                 155                 160

Asp Leu Gly Arg Asn Gln Leu Gln Ser Leu Pro Glu Gly Val Phe Asp
                165                 170                 175

Lys Leu Thr Gln Leu Lys Asp Leu Arg Leu Asp Ala Asn Gln Leu Lys
            180                 185                 190

Ser Val Pro Asp Gly Val Phe Asp Arg Leu Thr Ser Leu Gln Tyr Ile
        195                 200                 205

Trp Leu His Asp Asn Pro Trp Asp Cys Thr Cys Pro Gly Ile Arg Tyr
    210                 215                 220

Leu Ser Glu Trp Ile Asn Lys His Ser Gly Val Val Arg Asn Ser Ala
225                 230                 235                 240

Gly Ser Val Ala Pro Asp Ser Ala Lys Cys Ser Gly Ser Gly Lys Pro
                245                 250                 255

Val Arg Ser Ile Ile Cys Pro Thr
            260

<210> SEQ ID NO 10
<211> LENGTH: 264
<212> TYPE: PRT
<213> ORGANISM: Artificial Sequence
<220> FEATURE:
<223> OTHER INFORMATION: Repebody-rRE9

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

-continued

```
Leu Lys Glu Leu Thr Asn Leu Thr Tyr Leu Gln Leu Thr Pro Asn Gln
                85                  90                  95

Ser Leu Pro Asn Gly Val Phe Asp Lys Leu Thr Asn Leu Lys Glu Leu
            100                 105                 110

Ile Leu Pro Leu Asn Gln Leu Gln Ser Leu Pro Asp Gly Val Phe Asp
        115                 120                 125

Lys Leu Thr Asn Leu Thr Tyr Leu Asn Leu Ala His Asn Gln Leu Gln
    130                 135                 140

Ser Leu Pro Lys Gly Val Phe Asp Lys Leu Thr Asn Leu Thr Glu Leu
145                 150                 155                 160

Asp Leu Ser Tyr Asn Gln Leu Gln Ser Leu Pro Glu Gly Val Phe Asp
                165                 170                 175

Lys Leu Thr Gln Leu Lys Asp Leu Arg Leu Val Phe Asn Gln Leu Lys
            180                 185                 190

Ser Val Pro Asp Gly Val Phe Asp Arg Leu Thr Ser Leu Gln Tyr Ile
        195                 200                 205

Trp Leu His Asp Asn Pro Trp Asp Cys Thr Cys Pro Gly Ile Arg Tyr
    210                 215                 220

Leu Ser Glu Trp Ile Asn Lys His Ser Gly Val Val Arg Asn Ser Ala
225                 230                 235                 240

Gly Ser Val Ala Pro Asp Ser Ala Lys Cys Ser Gly Ser Gly Lys Pro
                245                 250                 255

Val Arg Ser Ile Ile Cys Pro Thr
            260

<210> SEQ ID NO 11
<211> LENGTH: 264
<212> TYPE: PRT
<213> ORGANISM: Artificial Sequence
<220> FEATURE:
<223> OTHER INFORMATION: Repebody-rRF1

<400> SEQUENCE: 11

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Gln Leu Thr Pro Asn Gln
                85                  90                  95

Ser Leu Pro Asn Gly Val Phe Asp Lys Leu Thr Asn Leu Lys Glu Leu
            100                 105                 110

Ile Leu Pro Leu Asn Gln Leu Gln Ser Leu Pro Asp Gly Val Phe Asp
        115                 120                 125

Lys Leu Thr Asn Leu Thr Tyr Leu Asn Leu Ala His Asn Gln Leu Gln
    130                 135                 140

Ser Leu Pro Lys Gly Val Phe Asp Lys Leu Thr Asn Leu Thr Glu Leu
145                 150                 155                 160

Asp Leu Thr Tyr Asn Gln Leu Gln Ser Leu Pro Glu Gly Val Phe Asp
                165                 170                 175
```

```
Lys Leu Thr Gln Leu Lys Asp Leu Arg Leu Tyr Gln Asn Gln Leu Lys
            180                 185                 190

Ser Val Pro Asp Gly Val Phe Asp Arg Leu Thr Ser Leu Gln Tyr Ile
        195                 200                 205

Trp Leu His Asp Asn Pro Trp Asp Cys Thr Cys Pro Gly Ile Arg Tyr
    210                 215                 220

Leu Ser Glu Trp Ile Asn Lys His Ser Gly Val Val Arg Asn Ser Ala
225                 230                 235                 240

Gly Ser Val Ala Pro Asp Ser Ala Lys Cys Ser Gly Ser Gly Lys Pro
                245                 250                 255

Val Arg Ser Ile Ile Cys Pro Thr
            260

<210> SEQ ID NO 12
<211> LENGTH: 264
<212> TYPE: PRT
<213> ORGANISM: Artificial Sequence
<220> FEATURE:
<223> OTHER INFORMATION: Repebody-F10

<400> SEQUENCE: 12

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Gln Leu Thr Pro Asn Gln
            85                  90                  95

Ser Leu Pro Asn Gly Val Phe Asp Lys Leu Thr Asn Leu Lys Glu Leu
        100                 105                 110

Ile Leu Pro Leu Asn Gln Leu Gln Ser Leu Pro Asp Gly Val Phe Asp
    115                 120                 125

Lys Leu Thr Asn Leu Thr Tyr Leu Asn Leu Ala His Asn Gln Leu Gln
130                 135                 140

Ser Leu Pro Lys Gly Val Phe Asp Lys Leu Thr Asn Leu Thr Glu Leu
145                 150                 155                 160

Asp Leu Thr Gly Asn Gln Leu Gln Ser Leu Pro Glu Gly Val Phe Asp
            165                 170                 175

Lys Leu Thr Gln Leu Lys Asp Leu Arg Leu Tyr Gln Asn Gln Leu Lys
        180                 185                 190

Ser Val Pro Asp Gly Val Phe Asp Arg Leu Thr Ser Leu Gln Tyr Ile
    195                 200                 205

Trp Leu His Asp Asn Pro Trp Asp Cys Thr Cys Pro Gly Ile Arg Tyr
210                 215                 220

Leu Ser Glu Trp Ile Asn Lys His Ser Gly Val Val Arg Asn Ser Ala
225                 230                 235                 240

Gly Ser Val Ala Pro Asp Ser Ala Lys Cys Ser Gly Ser Gly Lys Pro
            245                 250                 255

Val Arg Ser Ile Ile Cys Pro Thr
        260
```

-continued

```
<210> SEQ ID NO 13
<211> LENGTH: 266
<212> TYPE: PRT
<213> ORGANISM: Artificial Sequence
<220> FEATURE:
<223> OTHER INFORMATION: Repebody-A6

<400> SEQUENCE: 13

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Tyr Gly Ser Asp Ile Lys Ser Val Gln Gly Ile Gln Tyr Leu Pro Asn
    50                  55                  60

Val Arg Tyr Leu Val Leu Ser Arg Asn Lys Leu His Asp Ile Ser Ala
65                  70                  75                  80

Leu Lys Glu Leu Thr Asn Leu Thr Tyr Leu Glu Leu Lys Trp Asn Gln
                85                  90                  95

Leu Gln Ile Leu Pro Asn Gly Val Phe Asp Lys Leu Thr Asn Leu Lys
            100                 105                 110

Glu Leu Val Leu Asn Ser Asn Gln Leu Gln Ser Leu Pro Asp Gly Val
        115                 120                 125

Phe Asp Lys Leu Thr Asn Leu Thr Tyr Leu Asn Leu Ala His Asn Gln
    130                 135                 140

Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Leu
225                 230                 235                 240

Met Ser Ser Leu Met Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 14
<211> LENGTH: 266
<212> TYPE: PRT
<213> ORGANISM: Artificial Sequence
<220> FEATURE:
<223> OTHER INFORMATION: Repebody-B5

<400> SEQUENCE: 14

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Val Ala
        35                  40                  45
```

```
Ser Arg Ser Asp Ile Lys Ser Val Gln Gly Ile Gln Tyr Leu Pro Asn
    50              55                  60

Val Arg Tyr Leu Val Leu Ser Phe Asn Lys Leu His Asp Ile Ser Ala
 65              70                  75                      80

Leu Lys Glu Leu Thr Asn Leu Thr Tyr Leu Glu Leu Lys Trp Asn Gln
                85                  90                  95

Leu Gln Ile Leu Pro Asn Gly Val Phe Asp Lys Leu Thr Asn Leu Lys
                100                 105                 110

Glu Leu Val Leu Asn Ser Asn Gln Leu Gln Ser Leu Pro Asp Gly Val
                115                 120                 125

Phe Asp Lys Leu Thr Asn Leu Thr Tyr Leu Asn Leu Ala His Asn Gln
    130                 135                 140

Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
                165                 170                 175

Phe Asp Lys Leu Thr Gln Leu Lys Asp Leu Arg Leu Tyr Gln Asn Gln
                180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
                210                 215                 220

Arg Tyr Leu Ser Glu Trp Ile Asn Lys His Ser Gly Val Val Arg Leu
225                 230                 235                 240

Met Ser Ser Leu Met Ala Pro Asp Ser Ala Lys Cys Ser Gly Ser Gly
                245                 250                 255

Lys Pro Val Arg Ser Ile Ile Cys Pro Thr
                260                 265

<210> SEQ ID NO 15
<211> LENGTH: 266
<212> TYPE: PRT
<213> ORGANISM: Artificial Sequence
<220> FEATURE:
<223> OTHER INFORMATION: Repebody-H5

<400> SEQUENCE: 15

Glu Thr Ile Thr Val Ser Thr Pro Ile Lys Gln Ile Phe Pro Asp Asp
 1               5                  10                      15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
                35                  40                  45

Asn Asn Ser Asp Ile Lys Ser Val Gln Gly Ile Gln Tyr Leu Pro Asn
    50                  55                  60

Val Arg Tyr Leu Val Leu Ser Phe Asn Lys Leu His Asp Ile Ser Ala
 65              70                  75                      80

Leu Lys Glu Leu Thr Asn Leu Thr Tyr Leu Glu Leu Lys Trp Asn Gln
                85                  90                  95

Leu Gln Ile Leu Pro Asn Gly Val Phe Asp Lys Leu Thr Asn Leu Lys
                100                 105                 110

Glu Leu Val Leu Asn Ser Asn Gln Leu Gln Ser Leu Pro Asp Gly Val
                115                 120                 125

Phe Asp Lys Leu Thr Asn Leu Thr Tyr Leu Asn Leu Ala His Asn Gln
    130                 135                 140
```

-continued

```
Leu Gln Ser Leu Pro Asp Gly Val Phe Asp Lys Leu Thr Asn Leu Thr
145                 150                 155                 160

Gly Leu Glu Leu Cys Gly Asn Gln Leu Gln Ser Leu Pro Glu Gly Val
            165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Leu
225                 230                 235                 240

Met Ser Ser Leu Met Ala Pro Asp Ser Ala Lys Cys Ser Gly Ser Gly
            245                 250                 255

Lys Pro Val Arg Ser Ile Ile Cys Pro Thr
            260                 265
```